| United States Patent [19] | [11] | 4,044,060 |
|---|---|---|
| Buysch et al. | [45] | Aug. 23, 1977 |

[54] PROCESS FOR PREPARING GEMINAL DIHALIDES

[75] Inventors: Hans-Josef Buysch; Karl-Heinz Scholz, both of Krefeld, Germany

[73] Assignee: Bayer Aktiengesellschaft, Leverkusen, Germany

[21] Appl. No.: 685,558

[22] Filed: May 12, 1976

[30] Foreign Application Priority Data

June 7, 1975    Germany .............................. 2525442

[51] Int. Cl.$^2$ ...................... C07C 25/00; C07C 23/00
[52] U.S. Cl. ............................. 260/651 R; 260/590 D
[58] Field of Search ....................... 260/651 R, 590 D

[56] References Cited

U.S. PATENT DOCUMENTS

| 2,390,629 | 12/1945 | Weinmayr | 260/651 R |
| 2,994,653 | 8/1961 | Miller | 260/651 R |
| 3,715,407 | 2/1973 | Relles | 260/668 R |

*Primary Examiner*—Delbert E. Gantz
*Assistant Examiner*—J. Thierstein
*Attorney, Agent, or Firm*—Burgess, Dinklage & Sprung

[57] ABSTRACT

Geminal dihalides are prepared by reacting a non-enolizable aldehyde and/or ketone with phosgene or thionyl chloride in the presence of an organyl-phosphorus compound of 3-valent and/or 5-valent phosphorus.

8 Claims, No Drawings

PROCESS FOR PREPARING GEMINAL DIHALIDES

This invention relates to a process for the preparation of geminal dischlorides by reacting non-enolisable aldehydes and ketones with phosgene or thionyl chloride in the presence of organo-phosphorus compounds.

It is known from Liebig's Annalen der Chemie, Volume 70, pages 39 and 40 (1849) to react benzaldehyde with phosphorus pentachloride to give benzal chloride. However, this reaction has the disadvantage that phosphorus pentachloride, as a solid compound which sublimes and hydrolyses readily, can be handled only with difficulty and that separation of the phosphorus oxychloride formed frequently leads to difficulties when working up the reaction mixture. Working up or elimination of the phosphorus oxychloride formed proves to be very troublesome especially when the reaction is carried out industrially.

Furthermore, it is known from Liebig's Annalen der Chemie, Volume 626, pages 26 to 34 (1959) to react benzaldehyde with triphenylphosphine dichloride to give benzal chloride, but the yield is only 59%. When cyclohexanone is reacted with triphenylphosphine dichloride in the presence of an equimolar amount of triethylamine it is not the corresponding geminal dihalide which is obtained but 1-chlorocyclohex-1-ene in 45% yield (loc. cit., page 33).

Furthermore, it is known from U.S. Pat. No. 3,715,407 to react certain methyl ketones, such as acetophenone, with certain dichlorophosphoranes, such as dichlorotriphenylphosphorane, in acetonitrile to give geminal dichlorides, such as 1', 1'-dichloroethylbenzene, the triphenylphosphine oxide formed as a by-product being reconverted into the dichlorophosphorane by means of phosgene.

It is also known from Berichten der Deutschen Chemischen Gesellschaft, Volume 42, pages 3966 to 3985 (1909) to convert certain benzophenone derivatives into geminal dichloride by means of oxalyl chloride, phosgene or thionyl chloride; however, benzophenone itself cannot be converted in this way since electron-repellent substituents in the p-position are necessary in order to activate the carbonyl group.

None of these known processes enables geminal dichlorides to be prepared in a simple manner from non-enolisable carbonyl compounds.

SUMMARY

It has now been found that geminal dichlorides can be obtained from non-enolisable aldehydes and ketones in a simple manner by reaction with phosgene or thionyl chloride when the reaction is carried out in the presence of organyl-phosphorus compounds of 3-valent and/or 5-valent phosphorus.

DESCRIPTION

Examples which may be mentioned of organyl-phosphorus compounds which can be used in the process according to the invention are: di-organyl-halogenophosphines, tri-organyl-phosphines, tri-organyl-phosphonium salts, tri-organyl-phosphorus betaines, tri-organyl-phosphinealkylenes, 1,1-dihalogeno-tri-organyl-phosphines, 1-halogeno-1-acyl-tri-organyl-phosphines, 1-halogeno1-hydroxy-tri-organyl-phosphones, tri-organyl-phosphines, tri-organyl-phosphine oxides and tri-organyl-phosphine sulphides.

In general, the organo-phosphorus compounds containing 3-valent and/or 5-valent phosphorus which are used for the process according to the invention correspond to the formulae

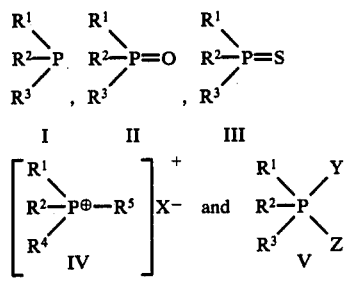

in which
R$^1$ and R$^2$ are identical or different and represent optionally substituted alkyl, aralkyl and aryl radicals and R$^1$ and R$^2$, conjointly with the phosphorus atom, can also form a 5-membered or 6-membered ring,
R$^3$ represents halogen or an optionally substituted alkyl, aralkyl or aryl radical,
R$^4$ represents an optionally substituted alkyl, aralkyl or aryl radical and, conjointly with R$^5$ and the phosphorus atom, can also form a 5-membered or 6-membered ring,
R$^5$ represents an optionally substituted alkyl, aralkyl, aryl or allyl radical,
X represents an anion, which, as an anionic group, can also be a substituent in one of the radicals R$^1$, R$^2$, R$^4$ or R$^5$, and
Y and Z are identical or different and represent halogen, a hydroxyl group, a carbonyloxyalkyl group, a carbonyloxyaryl group or a carbonyl chloride group. Halogens which may be mentioned are fluorine, chlorine, bromine and iodine, especially chlorine.

Alkyl radicals which may be mentioned are straight-chain and branched alkyl radicals with up to 12, prefeably up to 8 and especially up to 4, carbon atoms; preferred radicals which may be mentioned are methyl, ethyl, propyl, isopropyl, butyl, isobutyl, tert.-butyl, amyl and isoamyl.

Aralkyl radicals which may be mentioned are those with up to 18, preferebly up to 12 and especially up to 8, carbon atoms, the aliphatic part containing up to 9, preferably up to 6 and especially up to 4, carbon atoms, whilst the aromatic part preferably has 6, 10 and 14 carbon atoms; benzyl, phenylethyl, α,α-dimethylbenzyl and α-ethylbenzyl may be mentioned in particular.

Possible aryl radicals are those with up to 14 carbon atoms; phenyl and naphthyl may be mentioned in particular.

Possible substituents of the optionally substituted radicals R$^1$ to R$^5$ are all the groups which do not react under the reaction conditions; examples which may be mentioned are: halogen, the hydroxyl, nitro, cyano, carboxyl and isocyanate group and alkoxy, phenoxy and carbalkoxy radicals.

The scope of meanings for the alkoxy and carbalkoxy radicals corresponds, in respect of their alkyl radical, to that mentioned above for alkyl radicals.

Examples of anions X which may be mentioned are hydroxide, halide, sulphate and phosphate, but also alkoxylates, sulphonates and phosphonates; in general the anion X is not of particular significance; the choice of X depends on the ready availability of the corresponding phosphonium salt.

In addition, if one of the radicals R¹, R², R⁴ or R⁵ is a radical substituted by, for example, a carboxyl group or a sulphonic acid group, this carboxyl group or sulphonic acid group, as carboxylate or sulphonate, can also form the anion X.

Furthermore, phosphinealkylenes, such as can be obtained from the alkylphosphonium salts of the formula IV by splitting off HX, can be used as catalyst in the process according to the invention.

Examples of organo-phosphorus compounds which can be used as catalyst in the process according to the invention are: diphenylchlorophosphine, tributylphosphine, tris-cyanoethylphosphine, dicyclohexyldodecylphosphine, triphenylphosphine, tris-(p-chlorophenyl)-phosphine, 1-methyl-phospholine, triphenyl-benzyl-phosphonium chloride, tributyl-allyl-phosphonium bromide, triphenylphosphine-carbomethoxy-methylene, β-triphenylphosphonium propionate, phenyloxy-trimethylphosphonium chloride, β-triphenylphosphonium ethylsulphonate, triphenylphosphine hydroxide chloride, triethyl-carbonyloxyphenylchlorophosphine, 1,1-dichlorotriphenylphosphine, 1,1-dibromo-tricyanoethylphosphine, 1-phenyl-phospholine-(3)1,1-dichloride, dimethyl-cyclohexylphosphine oxide, trichloropropylphosphine oxide, dimethylphenylphosphine oxide, tri-(p-cyanophenyl)-phosphine oxide, triphenylphosphine sulphide, trimethylphosphine sulphide, 1-methyl-phospholine-(3)1-oxide and 1-phenyl-phospholine-(3)1-oxide.

Organyl-phosphorus compounds preferably used in the process according to the invention are: tributylphosphine, tri-(cyanoethyl)-phosphine, triphenylphosphine, tri-(4-chlorophenyl)-phosphine, triphenylphosphine oxide, triphenyl-benzyl-phosphonium chloride, β-triphenyl-phosphonium propionate and triphenylphosphine dichloride, especially triphenylphosphine, triphenylphosphine oxide and triphenylphosphine dichloride.

The distillation residue which contains the organophosphorus compound and which remains when the reaction mixture is worked up after the reaction has ended, is also a particularly preferred catalyst.

Of course, it is also possible to use mixtures of the abovementioned organo-phosphorus compounds.

In general, the organyl-phosphorus compound, according to the invention, is used in an amount of 0.001 to 0.2 mol per cent, preferably 0.005 to 0.15 mol per cent and especially 0.01 to 0.1 mol per cent, relative to the carbonyl compound employed.

Possible starting compounds for the process according to the invention are aliphatic aldehydes and ketones, cycloaliphatic ketones, alkylaryl and diaryl ketones which possess no further hydrogen atom in the α-position and contain the following groupings I – IV:

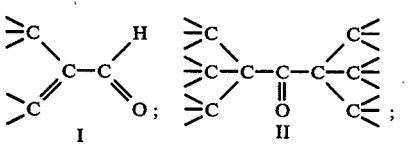

-continued

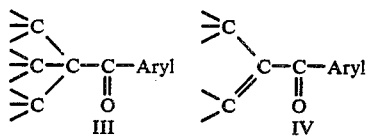

Appropriate starting compounds are especially compounds which contain the groupings I, III or IV, in particular compounds with the groupings I and IV, in which the carbonyl group is directly bound to an aromatic nucleus (grouping I), e.g. benzaldehyde and naphthaldehyde and their substituted derivatives, or is bound to two aromatic nuclei (grouping IV), e.g. optionally substituted benzophenone.

Examples of such compounds which may be mentioned are: α,α-dimethyl-phenylacetaldehyde, α,60 -dimethyl-p-nitrophenyl-acetaldehyde, di-tert.-butyl ketone, α,α,α',α'-tetramethyl-cyclohexanone, α,α,α-triphenylacetaldehyde, α,α-diphenyl-α-(p-cyanophenyl)-acetaldehyde, phenyl tert,-butyl ketone and phenyl α,α-dimethylbenzyl ketone, and also those compounds in which the α-hydrogen atoms are substituted by groups other than carbon atoms groups, for example α,α-dichloropropionaldehyde and α-chloroisobutyraldehyde; aromatic aldehydes, especially benzaldehyde and substituted benzaldehydes, examples of substituents which may be mentioned being halogen the nitro, cyano, isocyanato and carboxyl group, alkyl radicals, the phenyl and benzoyl radical and carboxyl, carbalkoxy, carbophenoxy and hydroxycarbonylalkyl group: optionally substituted aromatic aldehydes with several rings, such as naphthaldehydes and anthracenealdehydes, can also be used.

Diaryl ketones, such as benzophenone, dibenzoyl benzenes, fluorenone and anthrone, as well as diaryl α-diketones such as benzil, may also be mentioned.

In general, the process according to the invention is carried out without using a solvent; however, inert solvents or diluents, such as, for example, aliphatic, cycloaliphatic, araliphatic and aromatic hydrocarbons and halogenohydrocarbons as well as other inert functional derivatives of hydrocarbons can also be used as solvents; examples which may be mentioned are: benzine, for example benzine fractions with a boiling range between 60° and 200° C, cyclohexane, methylcyclohexane, tetrachloroethane, benzene, toluene, chloroform, carbon tetrachloride, chlorobenzene, dichlorobenzene, nitrobenzene, benzonitrile and benzotrichloride. It can also be advantageous to use the reaction products themselves, for example benzal chloride and α,α-dichloro-diphenyl-methane, as solvents.

The second reactant, that is to say phosgene or thionyl chloride, is employed in at least the stoichiometric amount of one mol per mol of carbonyl compound, but when the discontinuous procedure is used it is generally appropriate to use these readily accessible compounds, which can be separated off easily, in an excess of up to 15, preferably 6 and especially 1.2 to 4, mols.

If an adequate excess of thionyl chloride is used, this can serve at the same time as the solvent and/or diluent. Amounts of 20 to 50 mols of thionyl chloride per mol of carbonyl group to be chlorinated have proved suitable.

Using benzophenone as an example, the process according to the invention is illustrated by the reaction scheme which follows.

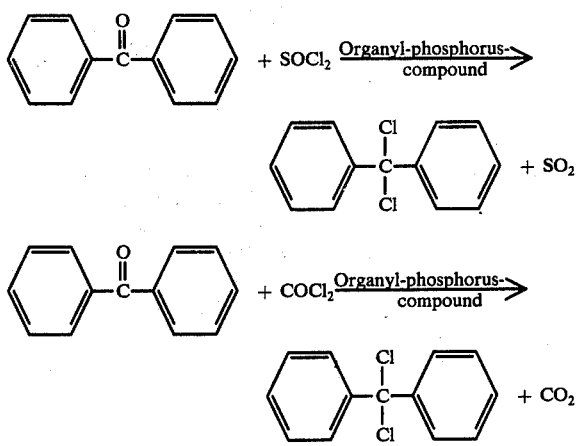

The procedure for carrying out the process according to the invention is simple; it can be widely varied according to the starting compound selected, the chlorinating agent and the organyl-phosphorus compound or the carboxylic acid amide.

In general, the process according to the invention is carried out under normal pressure, but it can also be carried out under elevated pressure, for example up to 30, preferably 10, bars.

The reaction temperature is also variable over a wide range and can be selected according to the reactivity of the chosen starting compound, for example between 0° and 300° C, preferably between 10° and 250° C and especially between 20° and 200°C.

When thionyl chloride is used the procedure followed can very simply be that the organyl phosphorus compound is initially introduced into thionyl chloride, which is in a larger or smaller excess depending on the solubility of the carbonyl compound in thionyl chloride, and the carbonyl compound is introduced at the reaction temperature. If the rate of reaction is relatively slow, it is also possible to combine the total amount of the carbonyl compound together with excess thionyl chloride and the organyl-phosphorus compound before the start of the reaction and to heat the mixture to the reaction temperature.

However, thionyl chloride can also be used in the gaseous form at tempertures above its boiling point, as is described below for phosgene.

When phosgene is used as the chlorinating agent it is possible, for example, in a simple manner to follow a procedure in which phosgene is fed in, at the reaction temperature, at the base of a vertical reaction tube which contains the carbonyl compound and the organyl phosphorus compound.

The process according to the invention can also be carried out continuously. When the continuous procedure is used, it is possible, by working in counter-current, in which case the reaction mixture is fed, in several successive reactors provided with gas distribution devices, such as frits or gassing stirrers, in the customary manner in counter-current to the chlorinating agent, that is to say thionyl chloride or phosgene, preferably phosgene, to achieve a virtually quantitive conversion in a single pass, so that only traces of thionyl chloride of phosgene are still present in the off-gas.

In all cases, excess thionyl chloride or phosgene, which evaporate from the reaction mixture at the selected reaction temperature, can, in a simple manner, be condensed by means of a reflux condenser fitted on the reactor or by means of a downstream cold trap and recycled, continuously or batchwise, into the reaction mixture. When an adequate amount of phosgene or thionyl chloride remains in the reaction mixture despite the loss on evaporation, the phosgene or thionyl chloride condensed in this way can also be used only in a later batch or in some other way.

The progress of the reaction can be followed in various ways, for example by continuous sampling and determination of the content of starting compound in the sample or by the evolution of $SO_2$. If the solvent has been used in which the carbonyl compound is only sparingly soluble but the chlorinated compound is readily soluble, the end of the reaction can also be recognised by the formation of a clear solution.

The sulphur dioxide which is evolved during the reaction can be collected in a known manner and rendered harmless as off-gas or, after appropriate purification, can be used for other purposes, for example for the preparation of sulphuric acid.

The reaction mixture can be worked up according to customary methods, by distillation or crystallisation, and appropriately the catalyst used is so selected that its properties enable it to be separated off easily.

The reaction mixture, which, in addition to the dihalide, can still contain residues of unreacted starting compound, sulphur dioxide and hydrogen chloride, is worked up in the customary manner by, for example, distilling off the products which have a lower boiling point that the desired dihalide, if appropriate under reduced pressure.

Of course, the organyl-phosphorus compound which is separated off can be used again; the process according to the invention can also be carried out both discontinuously and continuously.

In most cases, the dihalide obtained in this way is so pure that it can be further used without further purification. If purification should be necessary, this is carried out according to the customary methods, for example by distillation, if appropriate under reduced pressure, or by recrystallisation from a suitable solvent.

Because of their reactivity, the geminal dihalides obtained according to the process of the invention are important intermediate products for the preparation of dyestuffs, medicaments, agents for combating pests and plastics. In particular, they are used to synthesise bisphenols and polyphenols, which, in turn, are employed for the preparation of thermoplastic polyesters and polycarbonates.

The process according to the invention has the following advantages over the state of the art. In general, the reaction can be carried out without solvents, so that the reaction volumes are small. The by-products formed, that is to say $CO_2$ or $SO_2$, are gaseous at normal temperature and can be separated off easily; the problems arising with regard to environmental protection are minor. After cooling and washing out traces of HCl and phosgene, $CO_2$ can escape into the atmosphere and the absorption of $SO_2$ presents no particular problems according to the state of the art. The yields of geminal dichloride are high and the crude products are of sufficient purity for most application purposes, so that they do not have to be further purified. The small amounts of organyl-phosphorus compound or carboxylic acid amide contained in the products are not normally troublesome during further processing; if necessary they can be separated off easily in the customary manner and re-employed without loss of activity.

EXAMPLES 1 to 11

In each case, 182 g (1.0 mol) of benzophenone were reacted, in the presence of the catalyst, the nature and amount of which is indicated in Table I which follows, in a tube reactor 30 cm in length and 3.5 cm in diameter, into which phosgene was fed at the lower end through a frit and which had a take-off tube at the upper end for the $CO_2$ formed; the amount of phosgene employed was 130 g (1.3 mols) of phosgene per hour. Table I which follows also gives the reaction time, the conversion achieved in % of the benzophenone employed and the yield of $\alpha,\alpha$-dichloro-diphenyl-methane in % of theory, based on the conversion of benzophenone. The conversion and the yield were determined by gas chromatography.

Table I

| No. | Catalyst | Mols | Time hours | Temperature °C | Conversion % | Yield % of the conversion |
|---|---|---|---|---|---|---|
| 1 | $(C_6H_5)_3PO$ | 0.10 | 0.75 | 160–170 | 90 | 99 |
| 2 | $[(C_6H_5)_3P\oplus\text{—}CH_2CH_2COO\ominus]$ | 0.10 | 2 | 160–170 | 91 | 97 |
| 3 | $[(C_6H_5)_3P\oplus CH_2\text{—}\langle\rangle]\ Cl\ominus$ | 0.10 | 2 | 160–170 | 89 | 98 |
| 4 | $(NCCH_2CH_2)_3P$ | 0.10 | 3 | 150–160 | 61 | 95 |
| 5 | $(C_4H_9)_3P$ | 0.10 | 9 | 150–160 | 60 | 95 |
| 6 | $(Cl\text{—}\langle\rangle\text{—})_3P$ | 0.10 | 3 | 150–160 | 92 | 99 |
| 7 | $(C_6H_5)_3PO$ | 0.015 | 13 | 100–110 | 84 | 99 |
| 8 | $(C_6H_5)_3PO$ | 0.015 | 6 | 150–160 | 94 | 99 |
| 9 | $(C_6H_5)_3PO$ | 0.015 | 1 | 170–180 | 91 | 99 |
| 10 | $(C_6H_5)_3P$ | 0.015 | 2 | 180–190 | 99 | 99 |
| 11 | *) no catalyst | | 10 | 170–180 | no conversion | 0 |

*) Comparison Example

Some of Examples 1 to 11 were not carried out to complete conversion; they are intended to illustrate the relationship between the rate of reaction and the catalyst and the temperature.

EXAMPLE 12

210 g (1 mol) of benzil and 10.5 g (0.035 mol) of triphenylphosphine oxide are filled into the reaction tube described above and the mixture is treated, at about 130°–140° C, with about 90 g (0.9 mol) of phosgene gas per hour. After 11 hours, nitrogen is blow through the reaction mixture. The increase in weight of the reaction product is 55 g and the chlorine content of the crude product is 26.3% of Cl (calculated 26.8%). One carbonyl group in the benzil has been converted virtually quantitatively into dichloromethylene.

EXAMPLE 13

286.0 g (1.0 mol) of 1,4-dibenzoyl-benzene are filled, together with 5.7 g (0.02 mol) of triphenylphosphine, into the reaction tube described above and the mixture is treated, at about 150° to 160° C, for 10 hours with a stream of 130 g of phosgene gas per hour. This gives 395 g (about 99% of theory) of $\alpha,\alpha,\alpha',\alpha'$-tetrachlorodibenzylbenzene with a melting point of 90° to 91° C; 35.5% of Cl (calculated 35.8% of Cl).

EXAMPLE 14

286 g (1 mol) of 1,4-dibenzoylbenzene and 2.8 g (0.01 mol) of triphenylphosphine oxide are dissolved in 450 g of thionyl chloride and the mixture is boiled under reflux for 13 hours. After distilling off excess thionyl chloride and blowing nitrogen through the melt, 393 g (98% of theory) of $\alpha,\alpha,\alpha',\alpha'$-tetrachloro-p-dibenzylbenzene remain as a residue, which after cooling is almost colourless and crystalline; 35.4% of Cl (calculated 35.8% of Cl).

EXAMPLE 15

A mixture of 106 g (1 mol) of benzaldehyde, 2.8 g (0.02 mol) of triphenylphosphine oxide and 250 g of thionyl chloride were warmed to about 40° C and kept at this temperature. The evolution of gas has ceased after 4 hours.

Fractional distillation of the reaction mixture gives benzal chloride in quantative yield, as a colourless liquid, and a distillation residue of 3.5 g, which contains catalyst which can be used again.

EXAMPLE 16

A mixture of 106 g of benzaldehyde, the 3.5 g of distillation residue obtained according to Example 15 and 250 g of thionyl chloride is warmed to about 40° C and kept at this temperature. After 4 hours and the evolution of gas has ceased and the reaction mixture is subjected to fractional distillation.

Benzal chloride is obtained in quantitative yield as a colourless liquid.

EXAMPLE 17

151 g (1 mol) of p-nitrobenzaldehyde and 5 g (0.018 mol) of triphenylphosphine oxide are treated, in the tube reactor described above, at a temperature of 120° to 140° C, for 6 hours with 80 g (0.8 mol) of phosgene gas per hour. At the end of the reaction time the increased in weight was 53 g (calculated 55 g). Vacuum distillation of the resulting crude product gave, in a boiling range of 100° to 110° C/1.5 mm Hg, 177 g (86% of theory) of p-nitrobenzal chloride with a melting point of 44° to 46° C.

EXAMPLE 18

217 g (1 mol) of p-chlorobenzophenine and 13.9 g (0.05 mol) of triphenylphosphine oxide are treated, in the tube reactor described above, for 3 hours at about 160° C with 80 g (0.8 mol) of phosgene gas per hour. The increased in weight was 56 g (calculated 55 g). Vacuum distillation of the resulting crude product gave, in a boiling range of 127° to 131° C/0.3 mm Hg, 269 g (99% of theory) of p,$\alpha,\alpha$-trichlorodiphenylmethane as a pale yellow liquid; 38.8% of Cl (calculated 39.2% of Cl).

EXAMPLE 19

217 g of p-chlorobenzophenine and 13.9 g of triphenylphosphine oxide in 1,000 g of thionyl chloride are boiled under reflux until the evolution of SO$_2$ has ceased; this required about 10 hours. The reaction mixture was then subjected to fractional distillation. 244 g (90% of theory) of p,α,α-trichlorodiphenylmethane were obtained in a boiling range of 187° to 191° C/12 mm Hg.

EXAMPLE 20

227 g (1 mol) of m-nitrobenzophenone and 13.9 g (0.05 mol) of triphenylphosphine oxide were reacted, in the tube reactor described above, for 3 hours at about 160° C with 120 g (1.2 mols) of phosgene per hour and the resulting reaction product was then worked up by fractional distillation. 262 g (93% of theory) of m-nitro--α,α-dichlorodiphenylmethane with a melting point of 58° to 60° C were obtained in a boiling range of 160° to 170° C/0.5 mm Hg; 25.1% of Cl (calculated 25.13% of Cl).

EXAMPLE 21

227 g of m-nitrobenzophenone and 13.9 g of triphenylphosphine oxide in 1,000 g of thionyl chloride were boiled under reflux until the evolution of gas has ceased; the reaction time was about 11 hours. The reaction mixture was then subjected to fractional distillation. 251 g (89% of theory) of m-nitro-α,α-dichlorophenylmethane were obtained in a boiling range of 160° to 172° C/0.5 mm Hg.

EXAMPLE 22 (Comparison Example)

217 g (1 mol) of p-chlorobenzophenone in 1,000 g of thionyl chloride were boiled under reflux for 18 hours; no evolution of gas was observed. The thionyl chloride was then distilled off, the distillation finally being carried out in vacuo.

The residue has a melting point of 70° to 76° C and the chlorine content was found to be 17.0% of Cl.

In the literature a melting point of 75.5° to 76° C is quoted for p-chlorobenzophenone; the chlorine content is calculated as 16.4% of Cl.

The amount of the residue corresponded virtually quantitatively to that of the p-chlorobenzophenone employed.

EXAMPLE 23 (Use)

221 g of the 1,4-bis-(α,α-dichlorobenzyl)-benzene (I), prepared according to Example 13, are added dropwise in the course of 90 minutes, at 72° C, to a solution of 525 g of phenol and 300 ml of dioxane and the reaction mixture is then heated up to 124°–137° C and kept at this temperature for about 4 hours. After cooling, the crystal slurry is filtered off and the residue is washed with a dioxane/ligroin (1:2) solution and dried.

Yield of 1,4-bis-(4',4"-dihydroxy-triphenyl-methyl)-benzene (II): 292 g (83.6% of theory, based on crude 1,4-bis-(α,α-dichlorobenzyl)-benzene).

The product can be recrystallised, if necessary, from o-dichlorobenzene.

The reaction takes place according to the following equation:

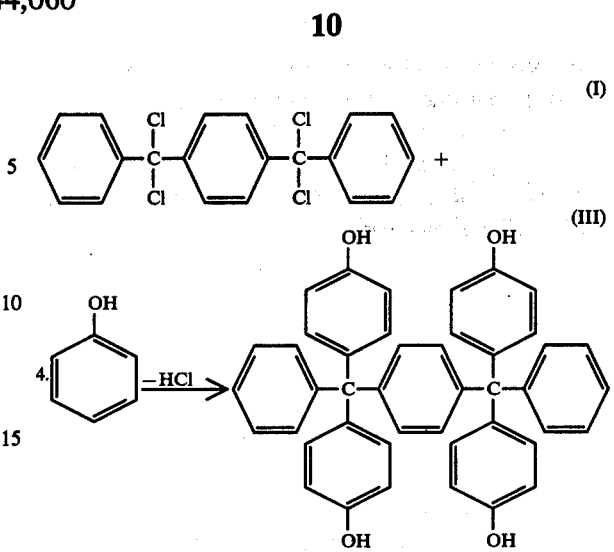

b. 1,825 g (18.5 mols) of phosgene are passed, in the course of 2 hours, at 24°–26° C, into a mixture of 3,420 g (15 mols) of bis-2-(4-hydroxyphenyl)-propane, 14.1 g (0.0224 mol = 0.15 mol %) of the 1,4-bis-(4',4"-dihydroxy-triphenylmethyl)-benzene prepared according to a), 67.5 g (0.45 mol = 3 mol %) of p-tert.-butylphenol, 4,300 g (48 mols) of 45% strength sodium hyroxide solution, 17,500 g of distilled water and 33,000 g of methylene chloride, whilst stirring. 6 g of triethylamine are then added.

After stirring for a further one hour, the organic phase is separated off, washed several times with 2% strength sodium hydroxide solution, 2% strength phosphoric acid and distilled water and finally worked up by adding chlorobenzene and distilling off the methylene chloride. On cooling the chlorobenzene solution, this gels and is further worked up in a granulating machine to give a powder/grain mixture. The resulting product is dried for 48 hours at 120° C in a water pump vacuum.

The relative viscosity of the product thus obtained is 1.340. The weight-average of the molecular weight determined by light scattering is 48,700.

What is claimed is:

1. Process for preparing geminal dichloride from a non-enolisable compound selected from the group consisting of aldehydes and ketones which comprises reacting said compound selected from the group consisting of aldehydes and ketones with phosgene or thionyl chloride in the presence of an organyl-phosphorus compound selected from the group consisting of di-organyl-halogenophosphine, tri-organyl-phosphine, tri-organyl-phosphonium salt, tri-organyl-phosphorus betaine, tri-organyl-phosphine alkylene, 1,1-dihalogeno-tri-organyl-phosphine, 1-halogeno-1-acyl-tri-organyl-phosphine, 1-halogeno-1-hydroxy-tri-organyl-phosphine, tri-organyl-phosphine oxide and tri-organyl-phosphine sulfide.

2. Process of claim 1 wherein the organyl-phosphorus compound is selected from the group consisting of triphenylphosphine, triphenylphosphine oxide and triphenylphosphine dichloride.

3. Process of claim 1 wherein the organyl-phosphorus compound is used in an amount of 0.001 to 0.2 mol per cent per mol of the compound selected from the group consisting of aldehydes and ketones.

4. Process of claim 3 wherein the organyl-phosphorus compound is used in an amount of 0.005 mol of 0.15 mol per cent per mol of the compound selected from the group consisting of aldehydes and ketones.

5. Process of claim 4 wherein the organyl-phosphorus compound is used in an amount of 0.01 to 0.1 mol per cent per mol of the compound selected from the group consisting of aldehydes and ketones.

6. Process of claim 1 wherein the reaction is carried out in a temperature range between 0° and 300° C.

7. Process of claim 6 wherein the reaction is carried out in a temperature range between 10° and 250° C.

8. Process of claim 7 wherein the reaction is carried out in a temperature between 20° and 200° C.

* * * * *

UNITED STATES PATENT AND TRADEMARK OFFICE
CERTIFICATE OF CORRECTION

PATENT NO. : 4,044,060
DATED : August 23, 1977
INVENTOR(S) : Hans-Josef Buysch and Karl-Heinz Scholz It is certified that error appears in the above-identified patent and that said Letters Patent are hereby corrected as shown below:

Col. 1, line 6, "dischlorides" should read -- dichlorides --.
Col. 1, line 66, "phosphones" should read -- phosphines --.
Col. 1, line 67, delete "tri-organyl-phospines" second occurrence.
Col. 2, line 42, "Prefeably" should read -- preferably --.
Col. 4, line 18, delete "60".
Col. 5, line 46, "tempertures" should read --temperatures--.
Col. 7, line 47, "blow" should read -- blown --.
Col. 8, line 42, delete "and" second occurrence.
Col. 8, line 61, "phenine" should read -- phenone --.
Col. 9, line 5, "phenine" should read -- phenone --.
Col. 10, line 7, "III" should read "II".
Col. 10, line 27, "hyroxide" should read -- hydroxide --.

Signed and Sealed this

Eighteenth Day of April 1978

[SEAL]

Attest:

RUTH C. MASON
Attesting Officer

LUTRELLE F. PARKER
Acting Commissioner of Patents and Trademarks